US00H002062H

(19) United States

(12) Statutory Invention Registration (10) Reg. No.: US H2062 H

Blaney et al. (43) Published: Apr. 1, 2003

(54) NURSING PAD

(75) Inventors: Carol Ann Blaney, Roswell, GA (US); Joseph George Neuwirth, Gainesville, GA (US)

(73) Assignee: Kimberly-Clark Worldwide, Neenah, WI (US)

(21) Appl. No.: 09/146,724

(22) Filed: Sep. 3, 1998

(51) Int. Cl.[7] ..... A61F 13/00

(52) U.S. Cl. ..... 602/46; 604/365

(58) Field of Search ..... 602/46; 604/365–367, 604/388, 378, 370, 384, 358, 374, 385.01, 385.07; 428/288, 290, 273

(56) References Cited

U.S. PATENT DOCUMENTS

| | | | | |
|---|---|---|---|---|
| 2,104,423 A | | 1/1938 | Hughes | |
| 2,630,119 A | | 9/1953 | Aagesen | 128/280 |
| 2,891,544 A | | 6/1959 | London | 128/280 |
| 2,896,623 A | | 7/1959 | Fitzgerald | 128/280 |
| 3,015,598 A | | 1/1962 | Jones | |
| 3,106,207 A | | 10/1963 | Dudley | |
| 3,262,451 A | | 7/1966 | Morse | 128/290 |
| 3,352,954 A | | 11/1967 | Smith | 264/90 |
| 3,356,090 A | | 12/1967 | Plantinga et al. | 128/280 |
| 3,417,755 A | | 12/1968 | Howard et al. | 128/516 |
| 3,442,268 A | | 5/1969 | Bird | 128/280 |
| 3,464,418 A | | 9/1969 | Silverman | 128/481 |
| 3,502,083 A | | 3/1970 | Howard et al. | 128/516 |
| 3,523,149 A | | 8/1970 | Hartmann | |
| 3,597,256 A | | 8/1971 | Young | |
| 3,597,800 A | | 8/1971 | Silverman | 264/292 |
| 3,805,790 A | | 4/1974 | Kaczmarzyk et al. | |
| 3,957,558 A | | 5/1976 | Lee et al. | |
| 4,013,750 A | | 3/1977 | Magidson et al. | 264/136 |
| 4,025,597 A | | 5/1977 | Sawamoto | 264/138 |
| 4,041,203 A | | 8/1977 | Brock et al. | 428/157 |
| 4,047,534 A | | 9/1977 | Thomaschefsky et al. | 128/461 |
| 4,074,721 A | * | 2/1978 | Smits et al. | |
| 4,100,324 A | | 7/1978 | Anderson et al. | 428/288 |
| 4,125,114 A | | 11/1978 | Repke | 128/280 |
| 4,164,228 A | | 8/1979 | Weber-Unger | 128/461 |
| 4,193,404 A | | 3/1980 | Repke et al. | 128/280 |
| 4,321,924 A | | 3/1982 | Ahr | |
| 4,372,098 A | | 2/1983 | Mason | |
| 4,397,644 A | | 8/1983 | Matthews et al. | |
| 4,400,227 A | | 8/1983 | Riemersma | |
| 4,404,052 A | | 9/1983 | Persson et al. | |

(List continued on next page.)

FOREIGN PATENT DOCUMENTS

| | | |
|---|---|---|
| EP | 0 205 242 | 12/1986 |
| EP | 0 214 867 | 3/1987 |
| EP | 0 665 315 | 8/1995 |
| EP | 0 698 385 | 2/1996 |
| GB | 2 268 687 | 1/1994 |
| WO | 93/16666 | 9/1993 |
| WO | 96/07376 | 3/1996 |
| WO | 96/19346 | 6/1996 |
| WO | 97/18346 | 5/1997 |

*Primary Examiner*—Michael J. Carone

(57) ABSTRACT

A nursing pad is disclosed having a liquid permeable body facing layer of a polyethylene/polypropylene bicomponent fiber web, an absorbent core comprising a composite fabric of thermoplastic fibers and an absorbent material, and a barrier laminate, such as a spunbond/meltblown/spunbond laminate or a spunbond/film laminate. The nursing pad can have a substantially concave shape, a thermally sealed edge and autogenous bonding to impart additional integrity to the three-dimensional shape.

29 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS 4,405,326 A 9/1983 Lenaghan
4,430,148 A 2/1984 Schaefer
4,531,999 A 7/1985 Persson et al.
4,610,750 A 9/1986 Mango
4,674,510 A 6/1987 Sneider ..... 128/481
4,675,012 A 6/1987 Rooyakkers
4,678,527 A 7/1987 Ulman
4,685,914 A 8/1987 Holtman
4,700,699 A 10/1987 Tollerud et al. ..... 128/156
4,701,177 A 10/1987 Ellis et al.
4,725,473 A 2/1988 Van Gompel et al.
4,729,371 A 3/1988 Krueger et al.
4,744,848 A 5/1988 Andrews et al.
4,756,949 A 7/1988 Spence et al. ..... 428/159
4,770,657 A 9/1988 Ellis et al.
4,777,073 A 10/1988 Sheth ..... 428/155
4,784,892 A 11/1988 Storey et al. ..... 428/172
4,823,783 A 4/1989 Willhite, Jr. et al.
4,850,991 A * 7/1989 Nakanishi et al.
4,886,697 A 12/1989 Perdelwitz, Jr. et al.
4,900,377 A 2/1990 Redford et al.
4,901,714 A * 2/1990 Jensen et al.
4,904,249 A * 2/1990 Miller et al.
4,913,957 A 4/1990 Strack et al. ..... 428/286
5,017,174 A 5/1991 Gowrylow ..... 450/37
5,059,277 A 10/1991 Willhite, Jr. et al.
5,082,720 A 1/1992 Hayes
5,104,396 A 4/1992 Oatley et al. ..... 604/379
5,141,805 A 8/1992 Nohara et al.
5,149,336 A * 9/1992 Clarke et al.
5,211,641 A * 5/1993 Roos et al.
5,213,881 A 5/1993 Timmons et al. ..... 428/224
5,236,430 A 8/1993 Bridges
5,284,703 A 2/1994 Everhart et al. ..... 428/283
5,298,321 A 3/1994 Isoda et al.
5,336,552 A * 9/1994 Strack et al. ..... 428/224
5,350,624 A 9/1994 Georger et al. ..... 428/219
5,382,400 A 1/1995 Pike et al. ..... 264/168
5,429,629 A 7/1995 Latimer et al.
5,464,688 A 11/1995 Timmons et al. ..... 428/298
5,470,639 A * 11/1995 Gessner et al.
5,486,166 A 1/1996 Bishop et al. ..... 604/366
5,490,846 A 2/1996 Ellis et al.
5,573,841 A 11/1996 Adam et al. ..... 428/219
5,607,798 A 3/1997 Kobylivker et al. ..... 442/381
5,652,051 A 7/1997 Shawver et al. ..... 442/362
5,653,702 A 8/1997 Brohammer et al. ..... 604/370
5,695,376 A * 12/1997 Datta et al.
5,695,868 A 12/1997 McCormack ..... 428/283
5,707,735 A * 1/1998 Midkiff et al.
5,830,296 A 11/1998 Emenaker et al.
5,843,062 A * 12/1998 Reidmiller
5,879,343 A * 3/1999 Dodge, II et al. ..... 604/378
5,989,688 A * 11/1999 Barge et al. ..... 428/198
6,049,024 A * 11/2000 Thomas et al.

* cited by examiner

NURSING PAD

FIELD OF THE INVENTION

The present invention relates generally to absorbent pads. More particularly, the present invention relates to improved nursing pads and methods of making the same.

BACKGROUND OF THE INVENTION

During the latter stages of pregnancy and after childbirth it is very common for mothers to produce excess milk resulting in various degrees of leakage. Although this problem may last generally throughout the entire nursing period, it is often most acute during the earlier stages of nursing. The leakage that results from this condition can seep through a brassiere and wet a mothers clothing. This is highly undesirable as it may contribute to mastitis, soil or stain the clothing as well as cause the mother discomfort in wearing wet clothing. Further, in many situations such as at work or in public, wetting of clothing can cause the mother unwanted embarrassment or stress. Thus, nursing pads have been developed to improve the comfort and confidence of nursing mothers. These pads are intended to absorb and retain leakage from a nursing mother and are placed adjacent the nipple and between the brassiere and breast. Various nursing pads are commercially available today. Examples of nursing pads are described in U.S. Pat. No. 4,047,534 to Thomaschefsky et al.; U.S. Pat. No. 3,356,090 to Plantinga et al.; U.S. Pat. No. 4,700,699 to Tollerud et al.; and U.S. Pat. No. 5,149,336 to Clarke et al.

Many nursing pads of the prior art suffer from one or more of the disadvantages described below. One such disadvantage is that the shape of the pad does not readily conform with the shape of the breast. When placed in the brassiere during use, the flat disc shaped pad is forced to conform to the cup shape of the breast and brassiere. However, in doing so the pad often bunches at one or more locations. Bunching of the pad contributes to leakage, can cause discomfort and also create unnatural or noticeable deformations which appear through the clothing. Further, flat nursing pads may also be prone to movement once in place which may result in bunching or an alignment that allows fluid to contact a mother's clothing. In addition, after absorbing fluid there is a tendency for some of the fluid to migrate to lower portions of the pad due to gravity. In this regard, many pads are assembled in such a manner that fluid may escape at the edge of the pad. Still further, the stitching, bonding and/or materials employed within nursing pads are often rough or exhibit poor hand.

Thus, there exists a need for an improved nursing pad with good absorbent properties and which has a pleasing feel against a woman's skin. Further, there exists a need for such a pad which is not prone to leak fluid through the edges of the pad and yet which does not have rough or stiff edges which may cause chaffing or irritation of the skin. Further, there exists a need for a nursing pad which will readily conform to the shape of the brassiere and breast without bunching. In addition, there exists a need for such a pad which, once in place, is not prone to movement or dislodging. There likewise exists a need for an improved breast pad which is both soft and durable while sufficiently inexpensive to be disposable.

SUMMARY OF THE INVENTION

The aforesaid needs are fulfilled and the shortcomings of the prior art overcome by an absorbent pad of the present invention which comprises a flexible absorbent pad having an inner liquid pervious layer, an absorbent core and an outer liquid impervious layer. The inner layer preferably comprises a liquid pervious nonwoven web of multicomponent thermoplastic fibers. Desirably the liquid pervious layer comprises a nonwoven web of bicomponent fibers such as, for example, fibers comprising a polyethylene polymer component and a polypropylene polymer component. One or more components of the multicomponent fibers of the liquid pervious nonwoven web can be hydrophilic. Additionally, the inner layer can be a point bonded and/or an autogenously bonded web. The individual layers of the absorbent pad are bonded together and, as an example, the layers of the pad can be bonded together along the edge and preferably are bonded with a continuous bond to create a sealed edge. In a further aspect, the absorbent pad can comprise a three-dimensionally shaped article having autogenously bonded thermoplastic fibers in both the inner and outer layers.

In still a further aspect of the invention, the absorbent core can comprise a stabilized matrix of thermoplastic fibers and absorbent material. In one embodiment, the absorbent core can comprise pulp, superabsorbent and a stabilizing matrix of thermoplastic fibers. In still a further aspect, the outer liquid impervious layer desirably comprises a multilayer laminate having at least one nonwoven web of thermoplastic fibers. As one example, the liquid impervious multilayer laminate can comprise a spunbond/meltblown/spunbond laminate. As a further example, the multilayer laminate can comprise a breathable microporous film and a nonwoven web. In a further aspect of the invention, the absorbent pad can have a three-dimensional contoured shape such as, for example, a generally concave shape.

DEFINITIONS

Figure 1:
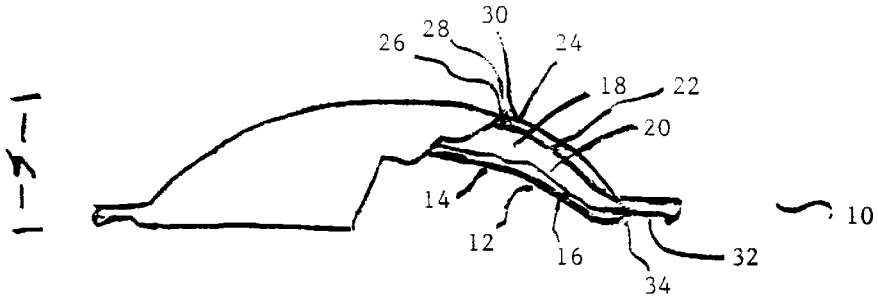
FIG. 1 is a side view of a nursing pad of the present invention with portions partially broken away to reveal the cross-section taken at A-A' of FIG. 2.

As used herein the term "nonwoven fabric" or "nonwoven web" means a web having a structure of individual fibers or threads which are interlaid, but not in an identifiable manner as in a knitted or meshed fabric. Nonwoven fabrics or webs have been formed from many processes such as for example, meltblowing processes, spunbonding processes, hydroentangling, air-laid and bonded-carded web processes.

As used herein the term "microfibers" means small diameter fibers having an average diameter not greater than about 10 microns. In a preferred embodiment the microfibers may have an average diameter of from about 0.5 microns to about 10 microns. Microfibers can include both meltblown fibers and/or fine spunbond fibers.

As used herein the term "spunbonded fibers" or "spunbond fibers" refers to small diameter fibers of oriented polymer. Spunbond fibers are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman; U.S. Pat. No. 3,542,615 to Dobo et al.; and U.S. Pat. No. 5,382,400 to Pike et al. Spunbond fibers are generally not tacky when they are deposited onto a collecting surface and thus often require additional mechanical or chemical bonding to form an integrated stabilized web.

As used herein the term "meltblown fibers" means fibers which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are generally carried by the high velocity gas stream and are deposited on a collecting surface to form a web of randomly disbursed meltblown fibers. Such a process is disclosed, for example, in U.S. Pat. No. 3,849,241 to Butin et al. and U.S. Pat. No. 5,213,881 to Timmons et al., the entire contents of which are incorporated herein by reference. Meltblown fibers are often microfibers which can be continuous or discontinuous and are generally tacky when deposited onto a collecting surface.

As used herein "multilayer nonwoven laminate" means a laminate comprising a plurality of layers wherein at least one of the layers is a nonwoven fabric. As an example, laminates wherein some of the layers are spunbond and some meltblown such as a spunbond/meltblown/spunbond (SMS) laminate and others as disclosed in U.S. Pat. No. 4,041,203 to Brock et al.; U.S. Pat. No. 5,169,706 to Collier et al.; U.S. Pat. No. 5,145,727 to Potts et al.; U.S. Pat. No. 5,178,931 to Perkins et al.; and U.S. Pat. No. 5,188,885 to Timmons et al.; the entire contents of which are incorporated herein by reference. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Multilayer laminates may also have various numbers of meltblown layers or multiple spunbond layers in many different configurations and may include other materials such as films (F), e.g. SMMS, SM, SF, SFS, etc.

As used herein, the term "coform material" means composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may be, for example, pulp, superabsorbent particles, cellulose and/or staple fibers. Coform processes are described in commonly assigned U.S. Pat. No. 4,818,464 to Lau; U.S. Pat. No. 4,100,324 to Anderson et al.; U.S. Pat. No. 5,284,703 to Everhart et al.; and U.S. Pat. No. 5,350,624 to Georger et al.; the entire contents of the aforesaid references are incorporated herein by reference.

As used herein a "superabsorbent" or "superabsorbent material" refers to a water-swellable, water-soluble organic or inorganic material capable, under favorable conditions, of absorbing at least about 10 times its weight and, more desirably, at least about 20 times its weight in an aqueous solution containing 0.9 weight percent sodium chloride. Organic materials suitable for use as a superabsorbent material in conjunction with the present invention include, but are not limited to, natural materials such as guar gum, agar, pectin and the like; as well as synthetic materials, such as synthetic hydroge polymers. Such hydrogel polymers include, for example, alkali metal salts of polyacrylic acids, polyacrylamides, polyvinyl alcohol, ethylene, maleic anhydride copolymers, polyvinyl ethers, methyl cellulose, carboxymethyl cellulose, hydroxypropylcellulose, polyvinylmorpholinone, and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres and the like. Typically the superabsorbent material is present within the absorbent body in an amount from about 5 to about 95 weight percent based on total weight of the absorbent body. Superabsorbents are generally available in particle sizes ranging from about 20 to about 1000 microns. An example of a suitable commercially available superabsorbent is SANWET IM 3900 available from Hoescht Celanese located in Portsmouth, Va. and DRYTECH 2035LD available from Dow Chemical Co. located in Midland, Mich.

As used herein the term "polymer" generally includes but is not limited to, homopolymers, copolymers, such as for example, block, graft, random and alternating copolymers, terpolymers, etc. and blends and/or modifications thereof. Furthermore, unless otherwise specifically limited, the term "polymer" shall include all possible spacial configurations of the molecule. These configurations include, but are not limited to, isotactic, syndiotactic and/or random symmetries.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, e.g. titanium dioxide for coloration, are generally present in an amount less than 5 weight percent and more typically about 2 weight percent.

As used herein the term "multicomponent fibers" or "conjugate fibers" refers to fibers which have been formed from at least two polymers extruded from separate extruders but spun together to form one fiber. Bicomponent fibers refer to a common, specific class of multicomponent fiber wherein the fiber comprises two distinct components. The polymers are arranged in substantially constantly positioned distinct zones across the cross-section of the fibers and extend continuously along the length of the fibers. The configuration of such a fibers may be, for example, a sheath/core arrangement wherein one polymer is surrounded by another or may be a side-by-side arrangement, a pie arrangement or an "islands-in-the-sea" arrangement. Conjugate fibers are taught in U.S. Pat. No. 5,108,820 to Kaneko et al.; U.S. Pat. No. 4,795,668 to Krueger et al.; and U.S. Pat. No. 5,336,552 to Strack et al. Multicomponent fibers are also taught in U.S. Pat. No. 5,382,400 to Pike et al. and may be used to produce crimp in the fibers by drawing the multicomponent fibers with heated air; the entire contents of the aforesaid patent is incorporated herein by reference. For bicomponent fibers, the polymers may be present in ratios of 75/25, 50/50, 25/75 or any other desired ratios. The fibers may also have shapes such as those described in U.S. Pat. No. 5,277,976 to Hogle et al.; U.S. Pat. No. 5,466,410 to Hills; and U.S. Pat. Nos. 5,069,970 and 5,057,368 to Largman et al., which describe fibers with unconventional shapes.

As used herein the term "multiconstituent fibers" or "biconstituent fibers" refers to fibers which have been formed from at least two polymers extruded from the same extruder as a blend. The term "blend" is defined below. Biconstituent fibers do not have the various polymer components arranged in constantly positioned distinct zones across the cross-sectional area of the fiber and the various polymers are usually not continuous along the entire length of the fiber, instead usually forming fibrils or protofibrils which start and end at random.

As used herein the term "blend" means a mixture of two or more polymers while the term "alloy" means a sub-class of blends wherein the components are immiscible but have been compatibilized.

As used herein, "ultrasonic bonding" means a process performed, for example, by passing the fabric between a sonic horn and anvil roll as illustrated in U.S. Pat. No. 4,374,888 to Bornslaeger.

As used herein "point bonded" means bonding one or more fabrics with a pattern of discrete bond points. As an example, thermal point bonding often involves passing a fabric or web of fibers to be bonded between a pair of heated bonding rolls. One of the bonding rolls is usually, though not always, patterned in some way so that the entire fabric is not bonded across its entire surface, and the second or anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern, having generally alternating perpendicular segments, with about a 19% bond area. Typically, the percent bonding area varies from around 10% to around 30% of the area of the fabric laminate web. Point bonding may be used to hold the layers of a laminate together and/or to impart integrity to individual layers by bonding filaments and/or fibers within the web.

As used herein, through-air bonding or "TAB" means a process of bonding a nonwoven multicomponent fiber web in which air which is sufficiently hot to melt one of the polymers of which the fibers of the web are made is forced through the web. The air velocity is between 100 and 500 feet per minute and the dwell time may be as long as 6 seconds. The melting and resolidification of the polymer provides the bonding. Through air bonding has relatively restricted variability and since through-air bonding (TAB) requires the melting of at least one component to accomplish bonding, it is often restricted to webs with two components like bicomponent fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments at contact points to integrate the web.

As used herein, the term "autogenous bonding" refers to bonding between discrete parts and/or surfaces independently of external additives such as adhesives, solders, mechanical fasteners and the like. As an example, multicomponent fibers may be autogenously bonded by through-air bonding whereby inter-fiber bonds develop at fiber contact points.

As used herein, the term "rib" means a ridge or wale in a fabric. An example of a rib is one of the parallel ridges in the surface of a fabric such as corduroy.

As used herein, the term "liquid impervious" means that a film, laminate or other fabric is relatively impermeable to the transmission of liquids, having a hydrohead of at least about 10 cm. Hydrohead as used herein refers to a measure of the liquid barrier properties of a fabric. The hydrohead test determines the height of water (in centimeters) which the fabric will support before a predetermined amount of liquid passes through. A fabric with a higher hydrohead reading indicates it has a greater barrier to liquid penetration than a fabric with a lower hydrohead. The hydrohead test can be performed according to Federal Test Method Standard 191A, Method 5514 or using a hydrostatic head tester available from Marlo Enterprises, Inc. of Concord, N.C. Unlike Method 5514, when using a hydrohead test the specimen is subjected to a standardized water pressure, increased at a constant rate until the first sign of leakage appears on the surface of the fabric in three separate areas. (Leakage at the edge, adjacent clamps is ignored.) Unsupported fabrics, such as a thin film, can be supported to prevent premature rupture of the specimen.

As used herein, the term "breathable" refers to a material which is permeable to water vapor having a minimum WVTR (water vapor transmission rate) of at least 300 $g/m^{2/24}$ hours. However, often applications of breathable barriers desirably have higher WVTRs and breathable barriers of the present invention can have WVTRs exceeding about 800 $g/m^{2/24}$ hours, 1500 $g/m^{2/24}$ hours or even exceeding 3000 $g/m^{2/24}$ hours. WVTR can be measured in accordance with ASTM Standard Test Method for Water Vapor Transmission of Materials, Designation E-96-80 as modified below and the results are reported in grams/square meter/24 hours. Circular samples measuring three inches in diameter were cut from each of the test materials and a control which was a piece of CELGARD™ 2500 film from Hoechst Celanese Corporation of Sommerville, N.J. CELGARD™ 2500 film is a microporous polypropylene film. Three samples were prepared for-each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32°C.) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed and immediately returned to the oven. After 24 hours, the pans were removed from the oven and weighed again. The preliminary test water vapor transmission rate values were calculated with Equation (I) below:

$$\text{Test WVTR}=(\text{grams weight loss over 24 hours})\times 315.5\ \text{g/m}^2/24\ \text{hours} \quad \text{(I)}$$

The relative humidity within the oven was not specifically controlled.

Under the predetermined set conditions of 100° F. (32° C.) and ambient relative humidity, the WVTR for the CELGARD™ 2500 control has been defined to be 5000 grams per square meter for 24 hours. Accordingly, the control sample was run with each test and the preliminary test values were corrected to set conditions using Equation (II) below:

$$\text{WVTR}=(\text{Test WVTR/control WVTR})\times(5000\ \text{g/m}^2/24\ \text{hours}) \quad \text{(II)}$$

DESCRIPTION OF THE PREFERRED EMBODIMENTS

In reference to FIG. 1, a nursing pad 10 is shown comprising a soft liquid pervious layer 12, an absorbent core 18 and a liquid impervious barrier laminate 24.

The nursing pad 10 has a generally concave shape such that the pad 10 may be place between the breast and a brassiere and readily conform thereto. The liquid pervious layer 12 is typically placed adjacent the breast, desirably centered about the nipple, such that the barrier laminate 24 is adjacent the brassiere. Fluids leaking from the breast will be drawn or wicked through the liquid pervious layer 12 and absorbed by the absorbent core 18. However, in reference to FIGS. 1 and 2, absorbed fluids will be retained within the absorbent core as they will not pass through the liquid impervious exterior layer 24 nor seep through the seal 34 of edge 32.

Existing personal care articles often employ a liquid pervious or body side layer which has a rough or unpleasant plastic feel. This is undesirable as it reduces the comfort of the person wearing the pad. Thus, the liquid pervious or body side facing layer of the present invention desirably comprises a material with good hand such as, for example, a nonwoven web of multicomponent fibers. In order to retain the desired level of liquid permeability, the multicomponent fibers should have high void spacing and a basis weight less than about 50 g/m$^2$, and more desirably between about 15 g/m$^2$ and 35 g/m$^2$. Desirably the liquid pervious layer comprises a nonwoven web, such as, for example, continuous spunbond fiber webs, bonded/carded webs, staple fiber webs and/or hydroentangled webs. Suitable materials for the liquid pervious layer include thermoplastic polymers such as polyolefins, polyamides (nylons), polyesters and copolymers and blends thereof. Multicomponent fibers allow the use of two or more polymers and, thus, the "hand" or feel of the nonwoven web may be improved by selecting at least one polymer with good hand. The second polymer, compatible and immiscible with the first, may comprise a polymer with better tensile properties or strength (relative to the first polymer). A particularly desired multicomponent fiber can comprise one or more components of an poly-ethylene polymer and one or more components of a polypropylene polymer. As an example, in one embodiment the liquid pervious layer may comprises either crimped or uncrimped bicomponent spunbond fibers having a polyethylene polymer sheath and a polypropylene polymer core.

The liquid pervious body side or skin facing layer 12 may comprise either hydrophilic or hydrophobic material, additionally the inner or skin facing layer can comprise both hydrophilic and hydrophobic components which desirably give the layer an overall hydrophilic character. As an example, the inner layer can comprise a nonwoven web comprising a mixture of hydrophilic and hydrophilic fibers. As a further example, the multicomponent fibers can comprise bicomponent fibers wherein the first component is hydrophilic and the second component is hydrophobic. The liquid pervious interior or skin side layer preferably promotes transfer of liquid away from the skin and does not retain fluid in order to improve the feel of the pad against the skin. Many thermoplastic polymers, including polyolefins, are inherently hydrophobic. Thus, in those instances where it is desired that the interior liquid pervious layer be hydrophilic the fibers may require treatment to impart wettability or hydrophilic properties to the fibers. Methods of treating polymers to make them hydrophilic are disclosed in U.S. Pat. No. 4,920,168 to Nohr et al.; U.S. Pat. No. 3,973,068 to Weber; and U.S. patent application Ser. No. 08/565,261 to Pike et al. In addition, known surfactants can be used to impart wettability to the fibers such as for example, octylphenoxy polyethoxy ethanol which is commercially available under the tradename TRITON X-102 from Union Carbide of Danbury, Conn. Polyolefin bicomponent fiber webs desirably comprise from about 2% to about 10% surfactant which is added to the polymer prior to extrusion. Once formed, the surfactant migrates to the surface of the fiber imparting wettability to the fiber.

Figure 4:
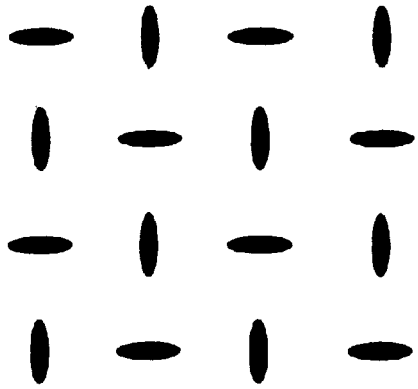
FIGS. 4 and 5 are views of bonding patterns suitable for use with the present invention.
Figure 5:
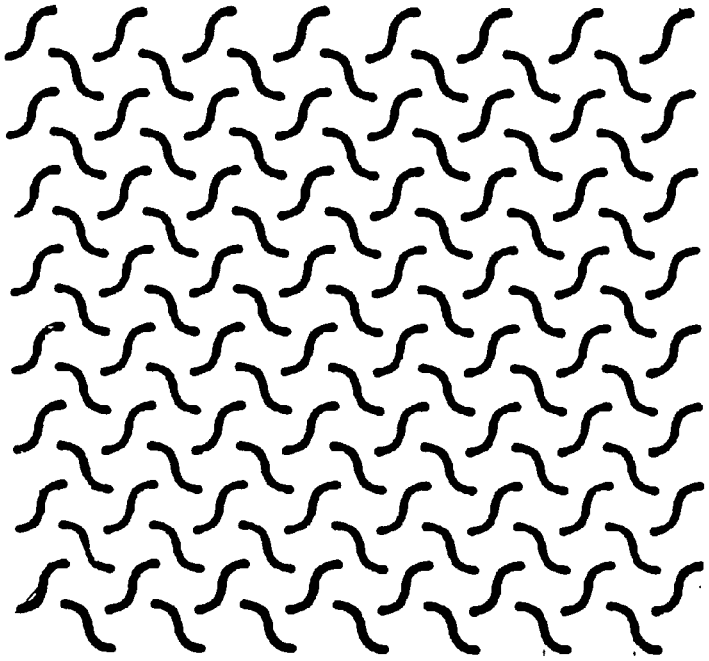

In addition, in order to impart the desired integrity to the body side or skin facing layer, the nonwoven web of multicomponent fibers can be bonded such as, for example, comprising autogenously bonded webs or point bonded webs. Bonding can be accomplished by through-air bonding (TAB), thermal point bonding, ultrasonic bonding or other known bonding techniques. In order to improve the hand of the article, point bonded fabrics desirably employ a repeating pattern of relatively small bond points. Examples of suitable patterns have been described herein above with regard to point bonding and are also shown in FIG. 4 and FIG. 5. Employing such a pattern is believed to create a fabric texture more pleasing to the touch, i.e. with improved hand.

Adjacent the liquid pervious layer 12 is an absorbent core which may comprise one or more layers capable of absorbing aqueous solutions or suspensions such as nursing milk.

The absorbent core 18 desirably comprises a combination or mixture of thermoplastic fibers and an absorbent material. The absorbent core can comprise coform materials although other suitable absorbent fabrics comprising a combination of thermoplastic fibers and absorbent material may likewise be used in accord with the present invention. Exemplary coform materials are disclosed in commonly assigned U.S. Pat. No. 5,284,703 to Everhart et al.; U.S. Pat. No. 5,350,624 to Georger et al.; and U.S. Pat. No. 4,100,324 to Anderson et al.; the entire contents of which are incorporated herein by reference. Suitable absorbent materials include, but are not limited to, fibrous organic materials such as woody or non-woody pulp such as cotton, rayon, recycled paper, pulp fluff and also include inorganic absorbent materials such as superabsorbent materials and/or treated polymeric fibers.

The absorbent core desirably has sufficient absorbent material to absorb at least about 3 g liquid and desirably from about 3 g to about 50 g liquid. In one embodiment the absorbent core 18 can comprise at least about 34 g/m$^2$ coform material, and more desirably comprises from about 68 g/m$^2$ to about 340 g/m$^2$ coform material. Further, the coform material preferably comprises from about 10% to about 35% by weight thermoplastic fibers. As one example, the coform material can comprise polypropylene meltblown fibers and wood pulp fibers. As a further example, the absorbent material may be held in a web of thermoplastic staple fibers such as, for example, air-laid or bonded-carded webs. The absorbent core may comprise one or more layers and additional absorbent materials may be dispersed within or between the one or more layers to increase the absorbency as desired. As an example U.S. Pat. No. 4,784,892 to Storey et al. teaches an absorbent material of meltblown fibers with an absorbent fibrous material (e.g. wood pulp) as well as superabsorbent dispersed therein; the contents of the aforesaid application is incorporated herein by reference. In addition, the absorbent core may comprise an absorbent layer of thermoplastic fibers and absorbent material wherein the weight percent of thermoplastic fibers to absorbent fibers varies or the pore size varies through the depth of the fabric.

The absorbent core is positioned between the liquid pervious layer 12 and an outer liquid impervious layer such as a multilayer nonwoven laminate 24. The multilayer nonwoven laminate is relatively impervious to the transmission of liquids and should have a hydrohead of at least about 10 cm or more and, even more desirably, has a hydrohead in excess of about 20 cm. In one embodiment, the multilayer nonwoven laminate can comprise a laminate of a first layer comprising at least a 6 g/m$^2$ layer of thermoplastic polymer microfibers and a second layer comprising at least an 8 g/m$^2$ layer of spunbond fibers; more desirably the multilayer laminate comprises from about 10 g/m$^2$ to 25 g/m$^2$ meltblown fibers and 15 g/m$^2$ to about 34 g/m$^2$ spunbond fibers. With such a two layer laminate the microfibers would preferably face the absorbent core and the spunbond fibers the opposed outer or distal side of the pad. The liquid impervious layer may also include additional layers and desirably the total basis weight of the barrier laminate is less than about 102 g/m$^2$ and even more desirably between about 20 g/m$^2$ and about 68 g/m$^2$. In a further embodiment the multilayer laminate can comprise a spunbond/meltblown/spunbond (SMS) laminate. Lower basis weight laminates, with good barrier properties such as disclosed in commonly assigned U.S. Pat. No. 5,492,751 to Butt et al., the entire content of which is incorporated herein by reference, are believed suitable for use in the present invention. In addition, in order to provide a nursing pad with overall improved hand the outer layer of the multilayer laminate can comprise a multicomponent fiber web, similar to those described above with regard to the inner or skin-facing layer. However, in order to help reduce slippage of the nursing pad an outer layer having a coarse, rough or tacky surface may be desirable.

In a further embodiment the multilayer nonwoven laminate or barrier laminate may comprise a microporous film/nonwoven laminate. One particularly useful barrier comprises a breathable stretched filled microporous film. Such films are typically filled with particles and then crushed and/or stretched to form a fine pore network throughout the film. The film-pore network allows gas and water vapor to pass through the film while acting as a barrier to liquids and particulate matter. The amount of filler within the film and the degree of stretching is controlled so as to create a network of micro-pores of a size and/or frequency to impart the desired level of breathability to the fabric. A suitable microporous film is disclosed in U.S. Pat. No. 4,777,073 to Sheth. An exemplary stretched filled film is also described in commonly assigned WO patent application 95/16562 and U.S. Pat. No. 5,695,868 to McCormack which discloses a stretched filled film comprising a predominantly linear polyolefin polymer, a bonding agent and about 30 to 80% by weight calcium carbonate which can be stretched to impart breathability to the film; the aforesaid application and patent are incorporated herein by reference. The stretched film may then be laminated to a nonwoven web to create a laminate that takes advantage of the strength and integrity of the nonwoven web and also the barrier properties of the stretched film. A further suitable laminate is disclosed in commonly assigned WO Patent Application 96/19346 to McCormack et al. and U.S. patent application Ser. No. 08/882,712 to McCormack et al. which employs a multilayer film having thin skin layers for providing improved bonding to a nonwoven support layer; the entire content of the aforesaid application is incorporated herein by reference. The nonwoven/film laminates allow thermal bonding of the laminate to the absorbent core and/or skin side layer while providing an article with good breathability and excellent barrier properties.

Figure 2:
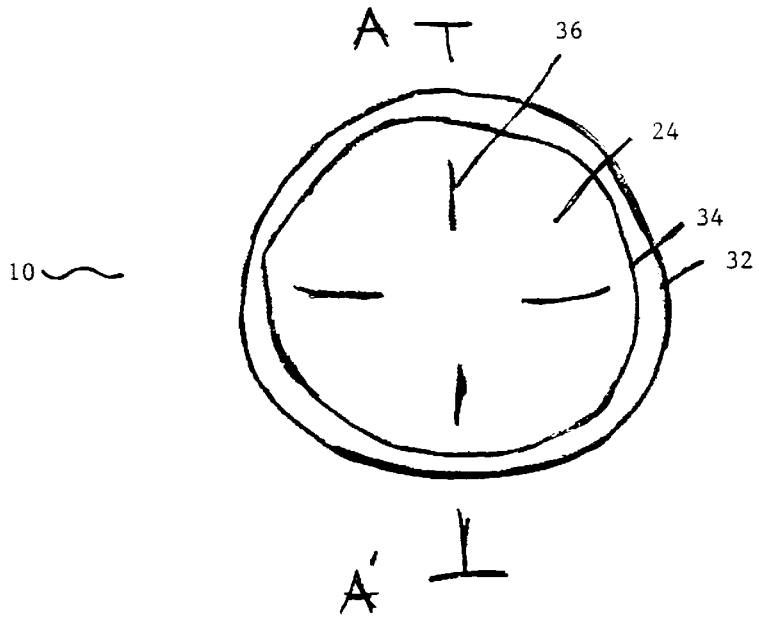
FIG. 2 is a top plan view of the nursing pad of FIG. 1.
Figure 3:
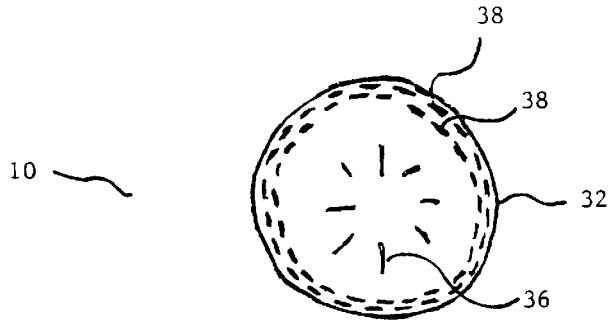
FIG. 3 is a top plan view of a nursing pad of the present invention.

The multiple layers of the nursing pad are preferably bonded together along the edge 32 of the nursing pad 10. The multiple layers may be bonded such as, for example, by thermal bonding, ultrasonic bonding, mechanical crimping, stitching and/or adhesively bonded. Desirably the layers are bonded using a method which creates a seal by causing flow of polymer within one or more of the thermoplastic fibers of the laminate. Bonding the individual layers of the absorbent pad to create a seal can be achieved by various mean such as, for example, by bonding using thermal or ultrasonic energy in combination with pressure. However, it is important that the method of bonding does not destroy the overall hand and drape of the individual layers; excessive thermal or ultrasonic energy and pressure can create a relatively stiff and uncomfortable pad with poor hand. As each of the layers includes thermoplastic polymers therein, bonding along an edge 32 acts to create a seal which reduces and/or prevents fluid from seeping out through the pad itself. The edge may be bonded with a continuous seam, as shown in FIG. 2, or a series of closely spaced point bonds 38 such as, for example, shown in FIG. 3. Desirably the bond or seal 34 is positioned at the edge up to about 1 cm from the outer most edge of the pad. In addition, it is also possible that the absorbent core not extend completely to the pad edge 32 such that the seal 34 comprises a bond between the barrier layer 24 and body side layer 12. Further, it is also possible that the liquid pervious or body side layer wrap around the outside edge and over the barrier layer.

In order to improve the ability of the nursing pad to conform to the breast and brassiere the nursing pad desirably has, with respect to the body side, a generally concave shape. Desirably the nursing pad comprises a substantially circular concave disc having a diameter of from about 5 to about 15 cm and height (h) of from about 0.6 cm to about 7 cm. However, the concave nursing pad may comprise other molded forms and shapes such as, for example, a generally tear shaped pad. In addition, in reference to FIG. 2, the nursing pad may have a plurality of ribs 36 extending radially from about the center of the pad. The ribs within the pad can give the pad improved resistance to bunching in use. Desirably the ribs extend along the outer portion of the liquid impervious layer 24. However, imparting ribs to the absorbent material and/or liquid pervious layer may advantageously improve wicking of liquid to the outer portions of the absorbent core.

Figure 6A:
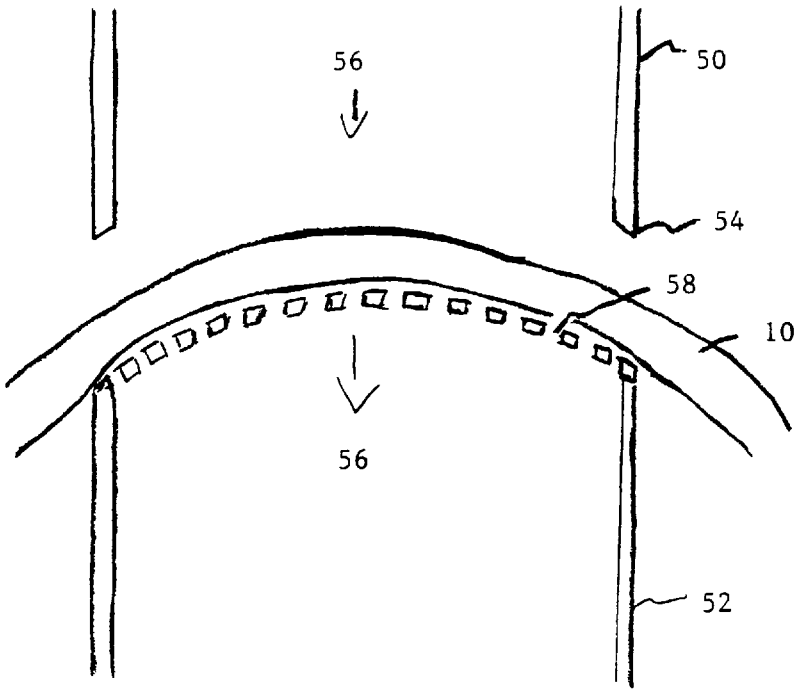
FIG. 6A is a cross-sectional view of an apparatus of FIG. 6 useful for making an absorbent pad of the present invention.
Figure 6:
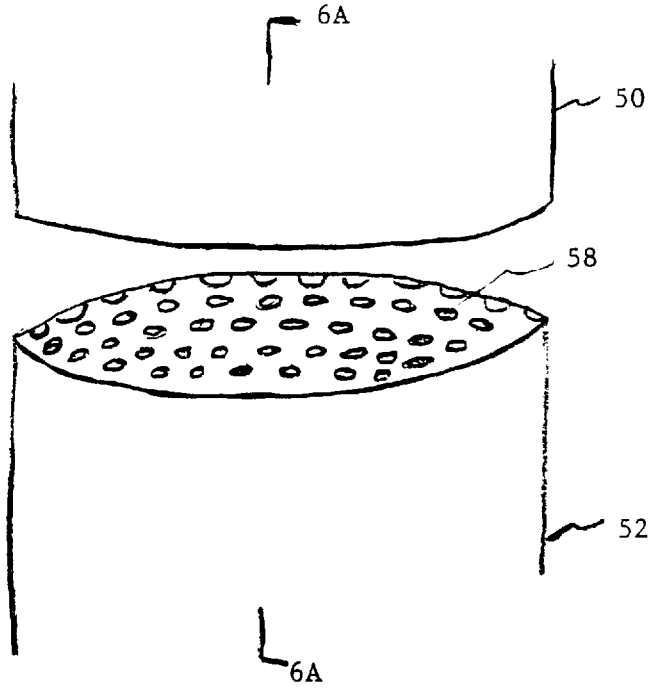
FIG. 6 is a side view of an apparatus useful for making an absorbent pad of the present invention.

The three-dimensional shape of the pad may be imparted by one of several methods. Desirably the nursing pad is molded or thermoformed into the desired shape. The nursing pad may be thermoformed in a manner to retain the good hand and softness of the thermoplastic layers such as described in U.S. Pat. No. 5,695,376; U.S. patent application No. 08/303,786 filed Sep. 9, 1994 to Dafta et al. and U.S. patent application No. 08/176,594 to Pike et al. filed Jan. 3, 1994; the entire contents of the aforesaid patent and applications are incorporated herein by reference. Thermoforming the nursing pad creates an autogenously bonded fabric which has the desired three-dimensional shape while having excellent flexibility and good hand. An article with superior hand may be achieved when thermoforming an article employing multicomponent fiber webs in the multilayer laminate of the liquid pervious layer and/or-the barrier laminate. In reference to FIGS. 6 and 6A, shaped cylinders 50 and 52 may be used to thermoform the absorbent pad 10 and simultaneously impart a seal to the pad edge. A raised ring or angled edge 54 upon the first cylinder 50 may be adapted to impart ultrasonic energy to the fabric thereby creating a sealed edge to the absorbent pad 10 upon pressing the first and second cylinders 50 and 52 against the fabric 10. Further, both cylinders can be hollow with cylinder 52 having foraminous surface 58 to allow heated air 56 to flow from first cylinder 50 to second cylinder 52 and through the fabric 10. The duration, pressure and energy imparted to the fabric can be varied to achieve the desired degree of bonding and overall integrity to the shaped pad. In addition, the nursing pad may be molded into the desired concave shape through use of one or more heated platens and/or molds. Desirably the platens can comprise a female base and a male forming plate having a patterned ring to impart the desired bond pattern to the pad edge. One or both of the platens may be heated although, desirably one or both of the plates are heated only at the pad perimeter. The layers comprising the pad may be placed between the platens with the barrier layer adjacent the female base. The platens may then be brought together at the desired pressure, temperature and duration to bond the layers together and impart an edge seal to the pad. Other methods of forming the shaped multilayer structure may also be used in conjunction with the present invention so long as they retain the good hand and drape of the individual materials and do not otherwise destroy the comfort or function of the pad.

While the invention has been described in detail with respect to specific embodiments thereof, and particularly by the examples described herein, it will be apparent to those skilled in the art that various alterations, modifications and other changes may be made without departing from the spirit and scope of the present invention. It is therefore intended that all such modifications, alterations and other changes be encompassed by the claims.

We claim:

1. An absorbent nursing pad, comprising:

an inner layer comprising a liquid pervious nonwoven web of continuous multicomponent thermoplastic fibers having a cross-section and a length formed from at least two polymers, said polymers are arranged in substantially constantly positioned distinct zones across the cross-section of the fibers and extend continuously along the length of the fibers; wherein said continuous multicomponent fibers are point bonded and at least one of said polymers is a polyolefin polymer;

an absorbent core comprising a stabilized matrix of polyolefin polymer fibers and absorbent material; and a liquid impervious multilayer laminate comprising a liquid barrier layer and an outermost layer, said outermost layer comprising a nonwoven web of thermoplastic polyolefin spunbond fibers and wherein said absorbent core is positioned between said inner layer and said liquid impervious multilayer laminate and further wherein said pad has a three-dimensional substantially concave shape and is peripherally bonded.

2. The absorbent nursing pad of claim 1 wherein said liquid pervious nonwoven web of multicomponent fibers comprises a web of bicomponent fibers.

3. The absorbent nursing pad of claim 2 wherein said bicomponent fibers comprise an ethylene polymer component and a propylene polymer component.

4. The absorbent nursing pad of claim 1 wherein the liquid impervious multilayer laminate comprises a spunbond/meltblown laminate.

5. The absorbent nursing pad of claim 1 wherein said liquid impervious multilayer laminate comprises a spunbond/meltblown/spunbond laminate.

6. The absorbent nursing pad of claim 5 wherein the outermost layer of the liquid impervious multilayer laminate comprises a nonwoven web of multicomponent spunbond fibers.

7. The absorbent nursing pad of claim 1 wherein said inner layer and said liquid impervious multilayer laminate are continously bonded together along the edge of said absorbent pad.

8. The absorbent nursing pad of claim 1 wherein the pad has a sealed edge.

9. The absorbent nursing pad of claim 2 wherein said absorbent pad has a flexible concave disc shape having a diameter between about 5 cm and 15 cm and a height less than about 7 cm.

10. The absorbent nursing pad of claim 1 wherein said absorbent material comprises pulp and superabsorbent.

11. The absorbent nursing pad of claim 1 wherein at least one component of the multicomponent fibers of said liquid pervious nonwoven web is hydrophilic.

12. The absorbent nursing pad of claim 2 wherein one component of the bicomponent fibers of said liquid pervious nonwoven web is hydrophilic and wherein the second component of the bicomponent fibers of said liquid pervious nonwoven web is hyrophobic.

13. The absorbent nursing pad of claim 2 wherein said bicomponent fibers comprise continuous spunbond fibers.

14. The absorbent nursing pad of claim 1 wherein said inner layer is point bonded.

15. The absorbent nursing pad of claim 13 wherein said bicomponent fibers are autogenously bonded.

16. The absorbent nursing pad of claim 1 wherein said absorbent pad has an edge and a substantially concave shape and further wherein said absorbent pad has autogenously bonded thermoplastic multicomponent fibers.

17. The absorbent nursing pad of claim 16 wherein said pad has a continuous bond proximate said edge.

18. The absorbent nursing pad of claim 17 wherein said continuous bond is contiguous with the edge of said pad.

19. The absorbent nursing pad of claim 16 having a diameter of between about 5 cm and about 15 cm and a height of less than about 7 cm.

20. The absorbent nursing pad of claim 1 wherein said multilayer laminate comprises a microporous film and a nonwoven web.

21. The absorbent nursing pad of claim 1 wherein said barrier laminate comprises a microporous film bonded on at least one side to a spunbond fiber web and further wherein the microporous film faces said absorbent core.

22. The absorbent nursing pad of claim 21 wherein said microporous film comprises a breathable filled polyolefin film.

23. The absorbent nursing pad of claim 20 wherein said microporous film comprises a filled polyolefin film having a basis weight less than 50 $g/m^2$.

24. The absorbent nursing pad of claim 20 wherein said pad has a sealed edge.

25. The absorbent nursing pad of claim 20 wherein said pad has a continuous bond proximate said edge.

26. The absorbent nursing pad of claim 20 wherein the fibers of said liquid pervious nonwoven web are autogenously bonded.

27. An absorbent nursing pad, comprising:

an inner layer comprising a liquid pervious nonwoven web of continuous multicomponent thermoplastic fibers having a cross-section and a length formed from at least two polymers, said polymers are arranged in substantially constantly positioned distinct zones across the cross-section of the fibers and extend continuously along the length of the fibers; wherein said continuous multicomponent fibers are point bonded, and at least one of said polymers is a polyolefin polymer; and the nonwoven web has a basis weight of less than about 50 $g/m^2$;

an absorbent core comprising a stabilized matrix of polyolefin polymer fibers and absorbent material having a basis weight from about 68 $g/m^2$ to about 340 $g/m^2$; and a liquid impervious multilayer laminate comprising a liquid barrier layer and an outermost layer, said outermost layer comprising a nonwoven web of thermoplastic polyolefin spunbond fibers having a basis weight of about 15 $g/m^2$ to about 34 $g/m^2$ and wherein said absorbent core is positioned between said inner layer and said liquid impervious multilayer laminate and further wherein said pad has a three-dimensional substantially concave shape and is peripherally bonded.

28. The nursing pad of claim 27, wherein the barrier layer comprises a nonwoven web of meltbown fibers having a basis weight of about 10 $g/m^2$ to about 25 $g/m^2$.

29. An absorbent nursing pad, comprising:

an inner layer comprising a liquid pervious nonwoven web of continuous multicomponent thermoplastic fibers having a cross-section and a length formed from at least two polymers, said polymers are arranged in substantially constantly positioned distinct zones across the cross-section of the fibers and extend continuously along the length of the fibers; wherein said continuous multicomponent fibers are point bonded, at least one of said polymers is a polyolefin polymer and said polymers are hydrophobic;

an absorbent core comprising a stabilized matrix of polyolefin polymer fibers and absorbent material; and a liquid impervious multilayer laminate comprising a liquid barrier layer and an outermost layer, said outermost layer comprising a nonwoven web of thermoplastic polyolefin spunbond fibers and wherein said absorbent core is positioned between said inner layer and said liquid impervious multilayer laminate and further wherein said pad has a three-dimensional substantially concave shape and is peripherally bonded.

* * * * *